United States Patent
Rodriguez Ponce

(10) Patent No.: US 9,283,052 B2
(45) Date of Patent: Mar. 15, 2016

(54) PLANNING MOVEMENT TRAJECTORIES OF MEDICAL INSTRUMENTS INTO HETEROGENEOUS BODY STRUCTURES

(75) Inventor: Maria Inmaculada Rodriguez Ponce, Munich (DE)

(73) Assignee: Brainlab AG, Feldkirchen (DE)

( * ) Notice: Subject to any disclaimer, the term of this patent is extended or adjusted under 35 U.S.C. 154(b) by 2671 days.

(21) Appl. No.: 11/858,961

(22) Filed: Sep. 21, 2007

(65) Prior Publication Data
US 2008/0082110 A1 Apr. 3, 2008

Related U.S. Application Data

(60) Provisional application No. 60/829,443, filed on Oct. 13, 2006.

(30) Foreign Application Priority Data

Sep. 28, 2006 (EP) .................................... 06020435

(51) Int. Cl.
*A61B 19/00* (2006.01)

(52) U.S. Cl.
CPC ............. *A61B 19/52* (2013.01); *A61B 19/2203* (2013.01); *A61B 19/50* (2013.01); *A61B 2019/2211* (2013.01)

(58) Field of Classification Search
CPC ............... A61B 19/52; A61B 19/2203; A61B 2019/2211; A61B 19/50
USPC ........... 318/432, 433; 382/128; 434/262, 263, 434/307 R; 600/411, 425, 424; 606/130
See application file for complete search history.

(56) References Cited

U.S. PATENT DOCUMENTS

| 5,492,131 | A | * | 2/1996 | Galel | A61M 25/0105 600/114 |
| 6,704,694 | B1 | * | 3/2004 | Basdogan | G06F 3/016 345/184 |
| 6,714,901 | B1 | * | 3/2004 | Cotin | B25J 9/1689 703/11 |
| 7,236,618 | B1 | * | 6/2007 | Chui | G09F 3/016 382/128 |
| 2002/0077797 | A1 | * | 6/2002 | Hall | 703/11 |
| 2002/0168618 | A1 | * | 11/2002 | Anderson et al. | 434/262 |

(Continued)

FOREIGN PATENT DOCUMENTS

DE 102 52 837 6/2004
WO 02/19243 3/2002

*Primary Examiner* — Stephen Holwerda
(74) *Attorney, Agent, or Firm* — Tucker Ellis, LLP; Patrick Clunk

(57) ABSTRACT

A method is provided for planning a position and/or a movement trajectory of a medical instrument in a heterogeneous body structure. The method includes providing at least one of a) body structure data corresponding to mechanical properties of the heterogeneous body structure, wherein said mechanical properties influence a movement of the instrument through the heterogeneous body structure due to the mechanical interaction between the instrument and the heterogeneous body structure, b) instrument data concerning mechanical and/or geometric properties of the instrument, or c) movement data concerning mechanical properties that are intended to cause and/or describe a movement of the instrument through the heterogeneous body structure. The position and/or movement trajectory-of the instrument or a probability that said position and/or movement trajectory will be achieved then is determined based on at least one of the movement data, the body structure data or the instrument data.

23 Claims, 5 Drawing Sheets

(56) References Cited

U.S. PATENT DOCUMENTS

| | | | |
|---|---|---|---|
| 2002/0183992 A1* | 12/2002 | Ayache | G06T 17/20 703/2 |
| 2004/0009459 A1* | 1/2004 | Anderson | G06F 19/3406 434/262 |
| 2004/0010221 A1 | 1/2004 | Pedain et al. | |
| 2004/0091845 A1* | 5/2004 | Azerad | G09B 23/283 434/263 |
| 2005/0116673 A1* | 6/2005 | Carl et al. | 318/432 |
| 2005/0131662 A1* | 6/2005 | Ascenzi | G09B 23/30 703/11 |
| 2005/0137531 A1 | 6/2005 | Prausnitz | |
| 2006/0084860 A1 | 4/2006 | Geiger et al. | |
| 2007/0129626 A1* | 6/2007 | Mahesh et al. | 600/407 |

* cited by examiner

PLANNING MOVEMENT TRAJECTORIES OF MEDICAL INSTRUMENTS INTO HETEROGENEOUS BODY STRUCTURES

RELATED APPLICATION DATA

This application claims priority of U.S. Provisional Application No. 60/829,443 filed on Oct. 13, 2006, which is incorporated herein by reference in its entirety.

FIELD OF THE INVENTION

The present invention relates to inserting instruments, such as catheters, syringes, biopsy needles, etc., into a body structure and, more particularly, into a biological tissue, such as organs, the brain and/or bones that exhibit a spatially differing rigidity, penetrability and/or elasticity.

BACKGROUND OF THE INVENTION

A heterogeneous body structure is a body structure that includes a plurality of different parts or different types of parts, wherein properties within one part of the body structure are different from properties of other parts of the body structure. Further, heterogeneous body structures exhibit spatial variation in the aforementioned properties. In other words, a heterogeneous body structure is in particular anisotropic.

Insertion of an instrument into a desired position within heterogeneous body structures can be difficult or impossible. The instrument can in particular be diverted from the desired and planned movement trajectory, in particular from the insertion trajectory of the instrument. This can be due to the heterogeneity and the consequent interaction, in particular mechanical interaction, between the heterogeneous tissue and the instrument.

Heterogeneous body structures occur in tumorous body structures, in particular in tumorous biological tissues, e.g., organs such as the brain or liver, for example. As can be established with the aid of elastography, for example, tumor cells are 5 to 28 times more rigid (less elastic) than healthy tissue cells. This can be measured using ultrasound elastography or MR elastography. When using instruments that are not completely rigid, such as for example a catheter, these rigid tumor regions increase the risk of the catheter not being able to reach the desired region. This can be caused by the instrument being diverted from its desired trajectory by tumor tissue, the instrument not being able to penetrate tumor tissue, or the instrument being bent or diverted such that the dispensing direction of a catheter, for example, is no longer in the planned direction. As a result, an injected drug may remain ineffective or can even cause damage at a non-planned location in healthy tissue. The same applies, for example, when using a biopsy needle that extracts samples from an incorrect region due to the needle being diverted by more rigid regions of the heterogeneous tissue. This can lead to misinterpretations in the physician's diagnosis.

SUMMARY OF THE INVENTION

The present invention enables an operator (e.g., a physician, surgeon, etc.) to better plan an incision into a heterogeneous body structure such that a probability that the planned or desired result can be increased.

A method is provided that allows regions in a body structure, in particular in a heterogeneous body structure, to be analyzed with regard to the risk of an instrument, for example a catheter such as an infusion catheter, being diverted or bent when said instrument or catheter is inserted into or through the tissue in question. In performing the method, information can be referenced that allows a statement of the elastic properties of the heterogeneous body structure, such as a target area (e.g., the tissue at the target location) to be ascertained. The target location is the location that is to be reached by the instrument.

Information such as, for example, a pressure distribution, strain distribution, distension distribution, displacement distribution and/or distortion distribution of the heterogeneous body structure, in particular the heterogeneous biological tissue, can also be used as the utilized information. One example is the local or non-local interstitial pressure.

Information on the instrument, in particular the mechanical properties of the instrument, also can be used. This information can be read or otherwise retrieved from a database in which mechanical information is registered or stored for the type of instrument (e.g., type of catheter or type of needle). This can include the geometric dimensions, elasticity or rigidity, the material of the instrument, etc.

All or some of the aforesaid information can be used to calculate the risk of an instrument being deviated or bent in the heterogeneous body structure, or to calculate the risk of the instrument, in particular a selected instrument, not being able to reach the target region. The trajectory to the target region, for example, can be blocked by a region of the heterogeneous body structure that is impenetrable by the instrument. Regions exhibiting a high or low risk of the instrument being bent, deviated and/or blocked when inserted are preferably displayed. Information on the mechanical properties of the heterogeneous body structure, such as its elastic and rigidity properties, can be spatially resolved or averaged for larger regions or indicated as a whole and used by the method described herein.

The mechanical properties of the heterogeneous body structure, in particular in the target region, can be expressed, for example, by elastic constants, the shear modulus, the elasticity modulus or Young modulus, distension constants, degrees of surface hardness of rigid structures, etc. The aforesaid variables represent or describe mechanical properties and can be used individually or in combination.

Information on the elastic properties, for example, can be gathered via magnetic resonance (MR) methods, ultrasound techniques or invasive, in-vitro or non-invasive methods, and gathered from the literature. Test probes, for example, can be inserted into the tissue to be examined or into tumorous samples, and their deviation can be detected in an image diagnosis. This also generally applies to determining other mechanical properties of the heterogeneous tissue. In-vitro methods can likewise be used to determine the mechanical properties of the tissue under observation, such as elastic properties and penetrability.

Mechanical properties of the instrument can likewise be determined by describing the material composition of the instrument and the materials that make up the instrument. The properties can be referenced in databases on the basis of the commercial name of the instrument, e.g., the type of catheter. The mechanical properties of the instrument also can be ascertained by corresponding tests.

The risk of the instrument being bent or diverted, or of a region not being penetrated by means of the instrument can be calculated on the basis of mathematical equations that describe the mechanical properties of the heterogeneous body structure, including in the target region. To this end, the mathematical equations can use the background pressure in the region of the heterogeneous body structure under observation, including the target region. This information can be related to a pressure exerted by the instrument in the region of the heterogeneous body structure under observation, including the target region.

The background pressure can include the natural pressure or represent the natural pressure formed by the tissue and its biological fluid content. The pressure in a healthy brain is typically 1 to 4 mm Hg. The pressure profile can be significantly heterogeneous, in particular in non-healthy tissue such as for example a tumor. The pressure in the center of a tumor, for example, is significantly different from the pressure at the edges of the tumor. If a catheter crosses or penetrates this region, it can experience a significant pressure gradient that can cause the catheter to bend. A spatial pressure profile over the tissue allows the pressure gradient to be determined and, thus, allows forces that can bend the catheter to be determined. In-vitro experiments, for example, can be used to determine a pressure profile within a tumor.

Corresponding forces, torques and/or energies that are present or exerted in the region of the heterogeneous body structure under observation and exerted by the instrument, can alternatively or additionally also be adduced and used in the method.

The risk of bending, deviating or of not penetrating can be calculated in a spatial differentiation, such that, for example, a distribution of the risk of deviating for the heterogeneous body structure under observation results. This can be displayed, for example, in color on a display by means of color variations.

The risk of deviation along a planned insertion trajectory of the instrument (e.g., a catheter trajectory) can be calculated on the basis of information on the mechanical properties of the heterogeneous body structure. The information can be spatially differentiated, wherein it is possible to take into account the fact that the mechanical properties of the instrument can be heterogeneous (e.g., not homogeneous) and can differ for example from section to section. The tip of the instrument, for example, can exhibit a different elasticity to the rear or back portion of the instrument.

The method can calculate a risk distribution that, for example, describes the risk of deviating, bending and/or not penetrating for a planned trajectory that the instrument is to travel in the heterogeneous body structure, in particular the target region. In this way, it is possible for a surgeon to assess whether the planned trajectory is promising or too risky. The details regarding the risk of the instrument deviating or bending and its spatial distribution in the heterogeneous body structure, in particular along the planned trajectory, also can be limited to a portion of the instrument, such as the instrument tip. This is of interest, for example, if a drug is to be dispensed in the target region by means of the instrument. In this case, the alignment of the dispensing opening of the instrument can be indicative of whether or not the drug will reach the desired region or not.

The method described herein relates generally to determining a position of an instrument, in particular a flexible instrument, in particular an elastic instrument. The instrument can change its shape, in particular bend, due to mechanical effects. Other examples of mechanical changes in shape are compressing and/or distending the instrument and/or buckling the instrument.

The aforesaid position of the instrument can include a spatial position of the instrument (e.g., the position of the region in which the instrument spatially occupies), the orientation of the instrument, the alignment of the instrument (e.g., an alignment of the active portion of the instrument, such as the tip of the instrument), the alignment of a dispensing opening of the instrument, the position of an incision area, the position of an extraction compartment in a biopsy needle, etc.

If the instrument is intended for drug injection, the drug injection direction can be calculated from a determined position of the injection opening. The position of the instrument as a whole can be taken into account in order to assess the distribution of the drug, in particular in order to assess the backflow of the drug along the instrument trajectory and the associated risk of the drug undesirably exiting the tissue onto the surface of an organ or being transported to undesired locations.

When performing the method, some of the information described below may be referenced. This information is referred to herein as "body structure data", "instrument data" and "movement data", each of which is preferably provided, in a spatial differentiation, for the heterogeneous body structure. It can differ from location to location and, in the case of movement data, can change over time.

The body structure data can describe mechanical properties of the heterogeneous body structure that have an effect on the movement of the instrument in the heterogeneous body structure. The movement of the instrument in the heterogeneous body structure may be influenced by a mechanical interaction between the instrument and the heterogeneous body structure. The body structure data allow the effect of the interaction on the movement to be determined.

Examples of such body structure data have already been mentioned above. The body structure data can be provided in a spatial differentiation. In particular, they can differ from location to location. Examples include:
  a) Deviating properties. These properties describe a deviation of the instrument when the instrument contacts the heterogeneous body structure, including locally at a point or region of the heterogeneous body structure. Deviations can be caused when a heterogeneous body structure exhibits a high rigidity or a low penetrability or is impenetrable for the instrument. The deviating properties can lead to the instrument slipping away on the hard surface or to the movement direction being tilted. Associated with the deviating properties are the bending properties mentioned below, which can likewise change a movement direction of the instrument. Physical variables for describing the deviating properties include the (local) hardness of the heterogeneous body structure, which, for example, can be described by a diamond pyramid hardness or Martens hardness, etc., or by its rigidity or elasticity.
  b) Shape-changing properties, in particular bending properties of the heterogeneous body structure are likewise caused by the hardness and/or rigidity and/or malleability, in particular the elasticity of the heterogeneous body structure. A malleability of the heterogeneous body structure when contacting an instrument that, for example, is bent can lead to a displacement of the movement trajectory of the instrument as compared to the case where the heterogeneous body structure is completely rigid. Depending on the malleability of the instrument, in particular its flexibility and ductility, different bends of the instrument along the movement trajectory can result when taking into account the movement data and instrument data. These bends can be calculated on the basis of equations that take into account the elasticity modulus of the instrument, geometric data of the instrument, forces and torques acting on the instrument and the aforesaid hardness and elasticity properties of the heterogeneous body structure. The curvature radius of a bend can depend on the elasticity moment and the torques acting on the instrument, and on the geometric characteristics of the instrument, including its diameter. The elasticity modulus (Young modulus) can be substantially influenced by the material of the instrument and can be different from section to section along the instrument. Other moduli include, for example, the compression modulus, distension modulus, shear modulus, torsion modulus, tension-distension diagrams, etc. These other moduli can describe the mechanical properties of the instruments or of the heterogeneous body structure. In particular, the other moduli can describe a change of shape of the instrument or the heterogeneous body structure. This change of shape is due to the effect of forces.

c) Blocking properties of the heterogeneous body structure, wherein the blocking properties describe mechanical properties that can stop a forward movement of the instrument in the heterogeneous body structure. The blocking properties can be described by the rigidity, penetrability and/or hardness of a region of a heterogeneous body structure. Degrees and definitions of hardness, such as for example the diamond pyramid hardness or Martens hardness, can likewise be used to describe the blocking properties. It is of course also possible to reference experimental data obtained by using instruments to test the penetrability of a biological tissue having comparable blocking properties (penetrability). In conjunction with the instrument data and movement data, it is then possible to determine whether the penetration of the instrument and the pressures and/or forces applied, for example, during the movement are sufficient to overcome the blocking properties of the heterogeneous body structure. It may in particular emerge that the instrument cannot overcome the blocking properties of the region and is thus blocked from moving further, for the given movement data. Alternatively, this can lead to the instrument buckling, which can likewise be calculated on the basis of instrument data, in particular the material data and characteristics of the instrument and the geometric data of the instrument. The latter can also be undesirable.

Examples of instrument data that determine mechanical and/or geometric properties of the instrument include:

a) data concerning the malleability of the instrument, including the elasticity, rigidity, hardness, distensibility, tensile strength and/or buckling resistance of the instrument;

b) data concerning the geometry, size and/or shape of the instrument, including data concerning the tip of the instrument and the shape of the tip, which can influence penetration of the instrument;

c) data concerning the material of the instrument that have a significant effect on the elasticity of the instrument, tensile strength of the instrument and on the penetration of the instrument.

Examples of movement data, which describe mechanical properties of the movement, include:

a) a starting location of the movement;

b) a target location of the movement;

c) a force that acts on the instrument in order to cause a movement in the heterogeneous body structure, including the direction of the force and/or the magnitude of the force, e.g., a vector of the force, and if the force is time-dependent, the force as a function of time, in particular the force vector as a function of time and the location of the point at which the force acts on the instrument as a function of time;

d) the pressure that acts on the instrument in order to cause a movement, in particular the direction and/or magnitude of the pressure. If the pressure is time-dependent, then also the time-dependency of the pressure, in particular the time-dependency of the pressure vector (e.g., the pressure vector as a function of time);

e) moments that act on the instrument in order to move it in the heterogeneous body structure, in particular torques and tilting moments that move the instrument in the heterogeneous body structure, in particular a vector of the moment as a function of time;

f) a movement trajectory that would result if the movement passed through a homogeneous, in particular resistance-free body structure. The movement trajectory can be described as a function of the position of the instrument dependent on time, in particular the position of the tip of the instrument dependent on time, wherein it can be assumed that the body structure exhibits a predetermined homogeneous viscosity, in particular that it is resistance-free. The influence of heterogeneous properties of the body structure on this movement trajectory, which may be referred to as an undisrupted movement trajectory, then can be calculated on the basis of the instrument data and body structure data.

The aforesaid body structure data, instrument data and movement data can be used to determine the position of the instrument in the heterogeneous body structure or to determine the probability that it will occupy this position. Preferably, mathematical equations are used that describe the mechanical interaction between the instrument and the heterogeneous body structure on the basis of the movement of the instrument which follows from the movement data. Examples of such equations are physical Newton equations and Lagrange equations for describing a movement, in which constraints are in particular taken into account that follow from the body structure data, instrument data and movement data.

With the aid of the aforesaid equations and on the basis of numerical methods, it is possible to determine a relationship between the position of the instrument in the heterogeneous body structure at the end of the movement and the position of the instrument at the start of the movement. The end of the movement can be characterized by the fact that a force is no longer acting on the instrument. This relationship can be calculated on the basis of the movement data, the body structure data and the instrument data and can be determined using numerical methods.

An operator, such as a physician or surgeon, preferably indicates a desired position of the instrument. On the basis of the aforesaid determined relationship, a nominal starting position then can be calculated that allows a desired position to be reached (if possible) or allows it to be reached with a particular probability, wherein multiple nominal starting positions may lead to the desired position. The instrument data can be varied on the basis of the aforesaid relationship, so as to optimally reach the desired position. The rigidity of the instrument can be varied to enable penetration into regions of the heterogeneous body structure that are difficult to penetrate. It is also possible to increase the elasticity of the instrument in order to reduce the danger of the instrument buckling and, thus, to reach the desired position along a bent trajectory. The instrument having a suitable elasticity, for example, then snakes along the rigid regions of the heterogeneous body structure to the desired position. On the basis of the relationship, the ideal movement data can be calculated (e.g., the expenditure of force and direction of force to be applied when driving the instrument forwards) in order to avoid penetrating rigid heterogeneous body structures, which may be undesirable. Further, the ideal movement data preferably enables the instrument to be driven forwards through the heterogeneous body structure by a sufficient expenditure of force.

An operator also can program a guiding mechanism (e.g., a robot arm) or an automatic or semi-automatic insertion aid, such that the movement data, instrument data and body structure data necessary for reaching a predetermined target or a portion of such data are used to reach a target area. Such automation can directly procure the corresponding data from the analysis device or the planning method. Movement data calculated in accordance with the method that result for particular ancillary conditions (constraints), e.g., the end position of the instrument and/or desired movement trajectory (at least desired sections of the movement trajectory) and/or avoiding particular regions during the movement and/or possible starting positions, are preferably referenced for guiding.

An expected movement trajectory of the instrument in the heterogeneous body structure is preferably described from a starting position to an end position. The starting position can be predetermined or may be determined as the nominal starting position as outlined above. The end position, in particular the desired position, however, also can be the position that results from a predetermined starting position. The movement trajectory can be calculated on the basis of the movement data, the body structure data and the instrument data. Mathematical equations that describe the mechanical interactions and as described herein can be used, wherein the movement data and/or body structure data and/or instrument data can be optimized such that a desired or acceptable movement trajectory, in particular to a desired end position (starting from a possible starting position) can be achieved. The risk of deviating from the expected movement trajectory is preferably indicated along the movement trajectory, e.g., the risk can be shown on a section by section basis. Alternatively or additionally, a probable movement channel can be indicated, within which the instrument will move with a predetermined probability.

The probabilities can be calculated on the basis of tolerances that apply to the movement data, body structure data and/or instrument data and thus ensure a level of certainty in calculating the movement trajectory. Examples are tolerances in reaching the starting position, tolerances in guiding the force that moves the instrument in the heterogeneous body structure, tolerances in the material constants and geometry of the instrument, tolerances in the rigidity and elasticity in regions of the heterogeneous body structure and the penetrability of the heterogeneous body structure, etc. The term "tolerances" here is also in particular intended to include the probability of deviating from an average value.

Also provided herein is a device that includes a data processing means designed to determine, in particular calculate using mathematical equations and/or numerical methods, the position of the instrument in the heterogeneous body structure or the probability of this position on the basis of the instrument data, the movement data and the body structure data. The device can comprise an input interface for inputting the aforesaid data. It also can include a database in which the aforesaid data are at least partially stored. It can likewise include a diagnostic unit, which, for example, is designed to detect body structure data by elastography. It can in particular include a monitoring unit, for example an x-ray apparatus, for monitoring the actual position of the instrument during the insertion process.

The device can be designed to identify deviations between the actual position of the instrument and the calculated position of the instrument (as most probable), output corresponding warning signals and/or generate a change in the movement data that guide the current insertion process. In particular, the device can comprise a mechanical guide that automatically guides the instrument in order to drive the instrument forward in the heterogeneous body structure. The device also can include the aforesaid instrument and a mechanical means for moving the instrument through the heterogeneous body structure.

BRIEF DESCRIPTION OF THE DRAWINGS

The forgoing and other features of the invention are hereinafter discussed with reference to the drawing.

DETAILED DESCRIPTION

Figure 1:
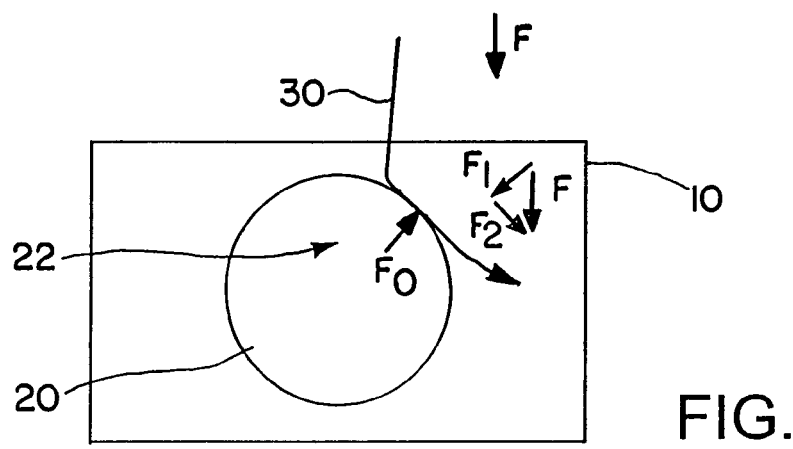
FIG. 1 shows exemplary effects of a heterogeneous body structure on the shape of an instrument.

FIG. 1 shows an exemplary heterogeneous body structure 10, an instrument 30 inserted into the heterogeneous body structure 10, and a region 20 in the heterogeneous body structure 10 which is highly rigid or difficult to penetrate. The region within the body structure 10 but outside the rigid region 20 should be easy to penetrate. In the region 22 of the rigid region 20, the instrument 30 is diverted and/or bent by the rigid region 20, wherein the instrument 30 is pushed forward by the force F. In accordance with the laws of vector addition, the force F can be divided into a force F1 and a force F2. The force F1 generates a corresponding counter force F0 in the region 22 of the heterogeneous body structure 10. This force F0 causes the instrument 30 to bend. In accordance with the laws of elasticity, the curvature of the bend is dependent on the elasticity modulus of the instrument 30 and on its geometric properties, in particular its diameter. The elasticity modulus depends in particular on the material of the instrument 30. The subsequent course of the movement of the instrument 30 in the heterogeneous body structure 10 can be calculated on the basis of curvature radius.

In the region 22 of the rigid region 20 of the heterogeneous body structure 10, it is also of course possible, depending on the shape-changing properties of the region 20, for the edge of the rigid region to be deformed. This deformation can be calculated and may influence the course of the movement trajectory of the instrument 30. FIG. 2a to 2g show examples of a possible movement progression, which can be calculated, predicted and in particular planned by the method described herein.

In each of the figures, the entry point of the instrument 30 into the heterogeneous body structure 10 is indicated by a circle 12. The cross "x" indicates the desired target region. In the example shown in FIG. 2a, the rigid region 20 of the heterogeneous body structure 10 is too rigid or impenetrable for the instrument 30 to penetrate. This problem could be overcome, for example, by changing the instrument data, e.g., increasing the penetration of the instrument, and/or the movement data (e.g., changing the force). However, without changing such parameters, the target area "x" in FIG. 2a cannot be reached, and this result can be calculated by the method described herein.

Figure 2A:
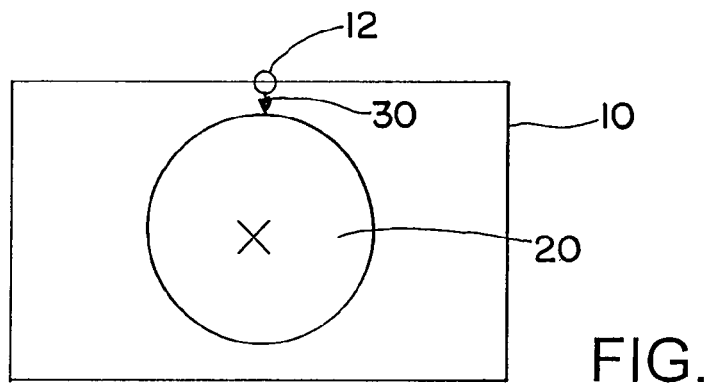
FIGS. 2a to 2g show examples in which the instrument reaches or does not reach the target area due to the interaction between the instrument and the heterogeneous body structure.
Figure 2B:
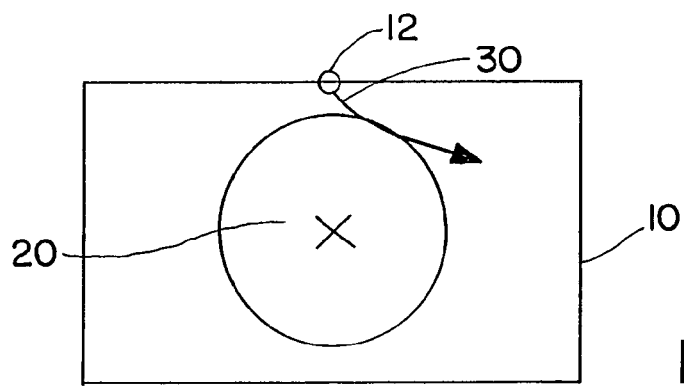

In the example shown in FIG. 2b, the instrument 30 is bent at the rigid region 20. Bending the instrument 30 results in a deviation of the tip of the instrument 30 away from the desired target area "x". If the instrument 30 is a catheter, then in this example the drug dispensed from the "bent" catheter would not reach the desired target region "x".

Figure 2C:
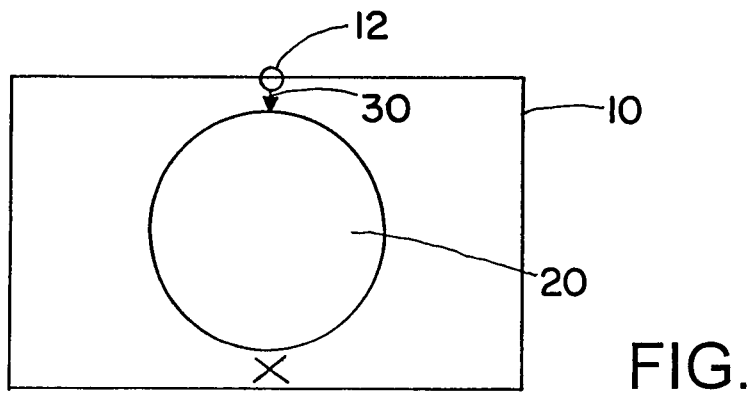

In the example shown in FIG. 2c, the rigid region 20 is likewise impenetrable, such that a surgeon cannot reach the target area "x" using a planned instrument 30 (using particular instrument data and movement data). In other words, the instrument is blocked from reaching the target region "x".

Figure 2D:
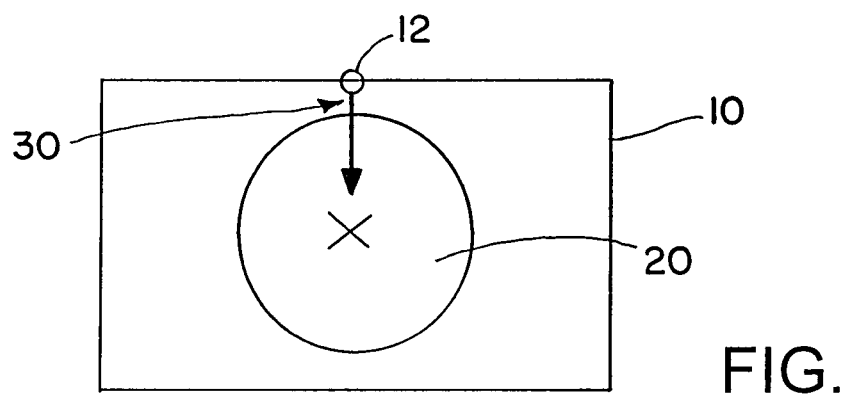

In FIG. 2d, an instrument 30 having suitable instrument data and suitable movement data has been selected with the aid of the method described herein in order to penetrate the rigid region 20 so as to reach the desired target location "x".

Figure 2E:
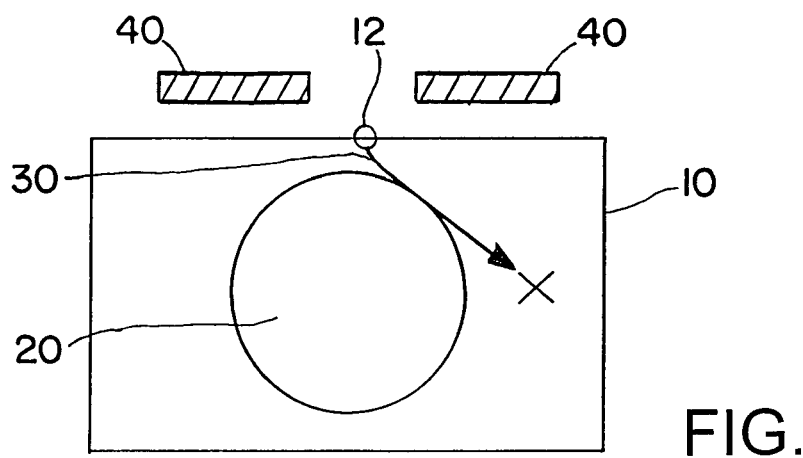

In the example of FIG. 2e, the instrument 30 is bent at the rigid region 20. The suitable entry point 12 and the suitable instrument data have been determined on the basis of the method described herein such that the instrument 30 bends at the rigid region 20 so as to reach the target region "x". This is even possible when the starting location 12 for the movement of the instrument 30 is only slightly variable, because barriers 40 prevent the instrument 30 from being inserted at a different location. Suitably selecting the instrument data, in particular a suitable elasticity of the instrument 30 (and movement data), then allows the instrument to reach the target region "x". In particular, elasticity data and geometric data of the instrument 30 can be calculated from the curvature radius of the instrument necessary for reaching the target point "x". On the basis of this, a suitable instrument can be (automatically) selected or proposed, wherein the selected or proposed instrument exhibits the appropriate characteristics. The instrument, for example, may be selected from a database comprising instrument characteristics.

Figure 2F:
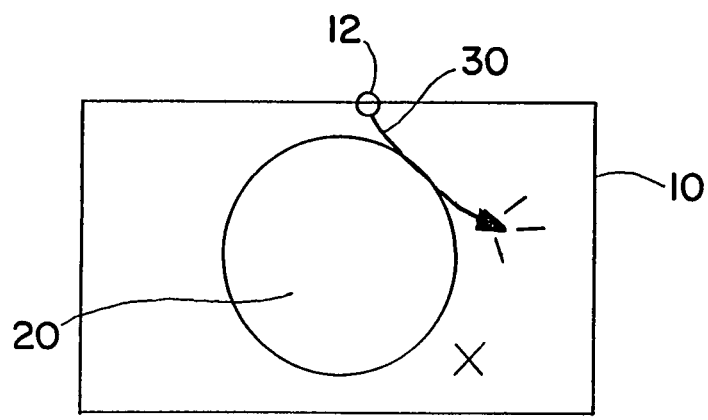

FIG. 2f shows an example in which an instrument 30 is diverted by the rigid structure 20 such that dispensing the drug through the instrument 30 misses the target area "x". The risk of such diversion and/or of the drug not reaching the target region can be calculated with the aid of the method described herein.

Figure 2G:
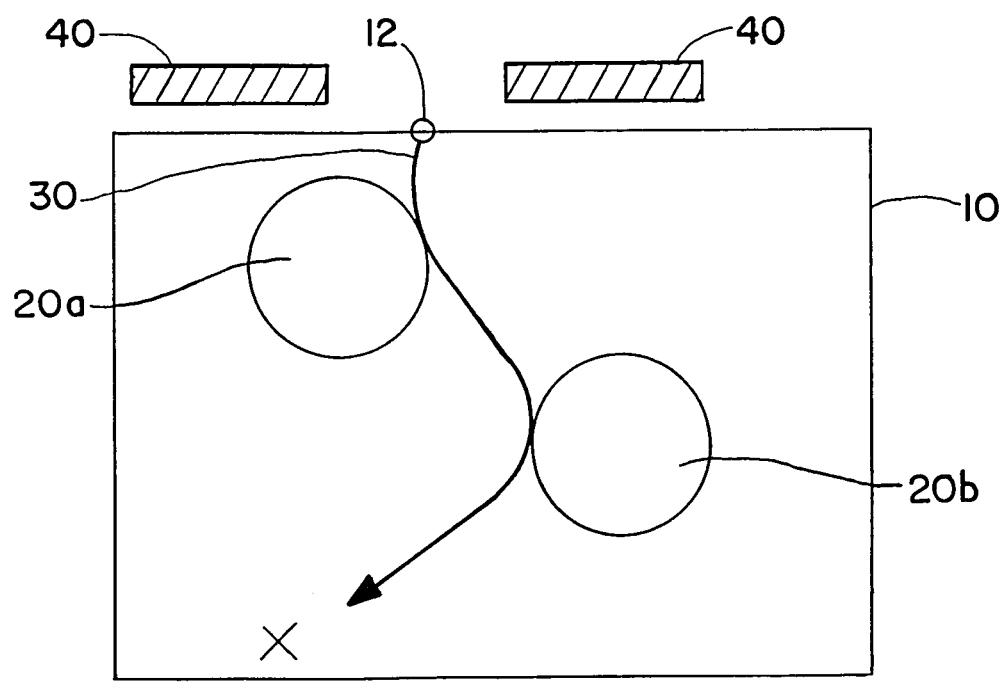

FIG. 2g shows an example of how an instrument can reach a desired target region "x" with the aid of the method described herein. Two rigid regions 20a and 20b are situated in the heterogeneous body structure 10. Possible starting locations for the movement are prevented by the barriers 40. A linear movement of the instrument 30 in FIG. 2g would lead to the instrument 30 hitting the rigid surface of the region 20a. Penetrating this surface is undesirable for medical reasons or would lead to undesirable instrument properties. A suitable ductility of the instrument can be calculated as described herein to achieve the desired movement trajectory to the target "x". In particular, an instrument having an appropriate elasticity can be selected, which leads to curvature radii in the bending of the instrument when it contacts the rigid regions 20a and 20b, such that the end of the movement trajectory matches the target region.

Figure 3:
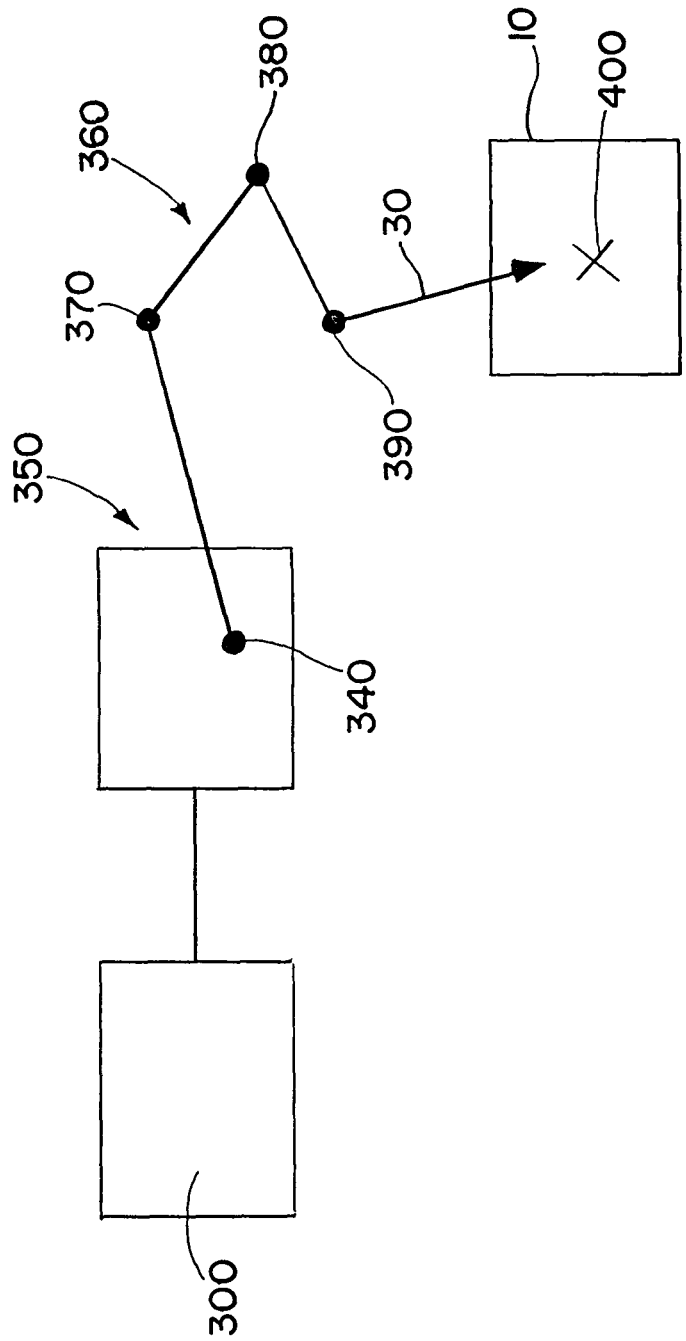
FIG. 3 shows an exemplary device in accordance with the invention for guiding an instrument through a heterogeneous body structure.

FIG. 3 shows an exemplary device for guiding an instrument through a heterogeneous body structure, in particular an instrument guiding device. A data processing means 300 (e.g., a computer) calculates movement data for guiding a guiding mechanism on the basis of the body structure data of the heterogeneous body structure 10, instrument data concerning an instrument 30 and a desired target area 400 and/or desired movement trajectory.

The guiding mechanism 350 can include a robot arm 360 comprising multiple joints 370, 380 and 390. The instrument 30 is held at one end 340 of the arm 360, and the robot arm 360 guides the instrument through the heterogeneous body structure to the desired target area 400 based on the calculated movement data for the movement along a movement trajectory.

Figure 4:
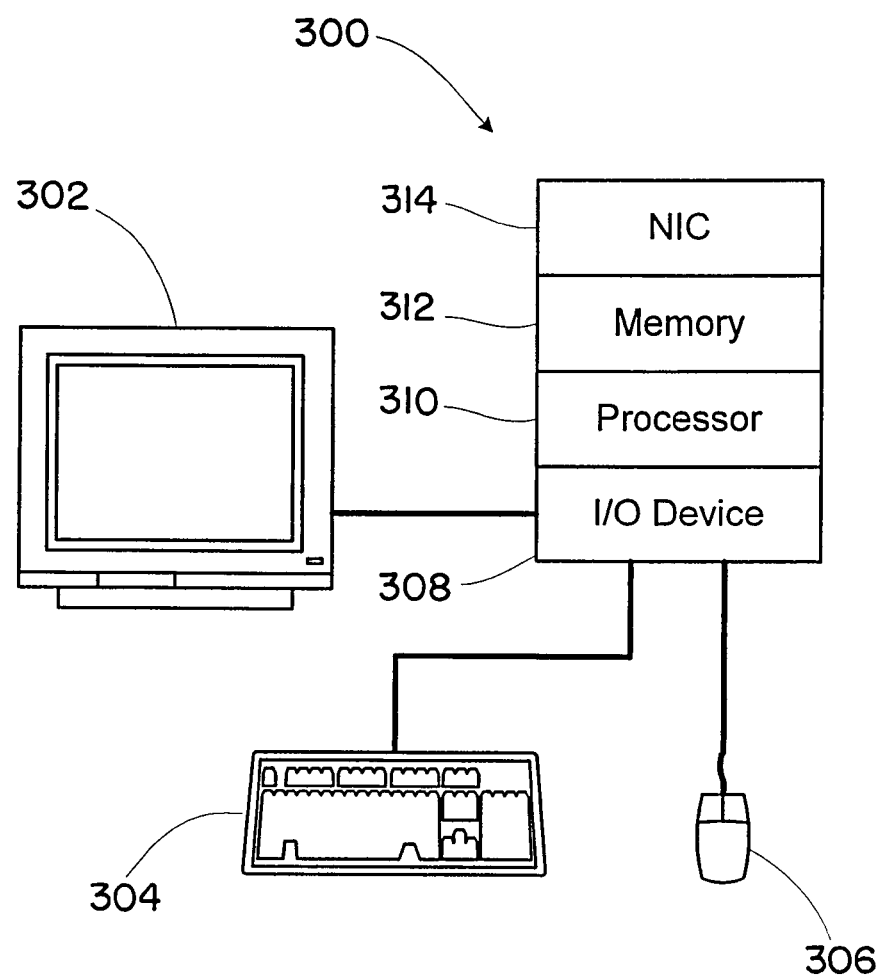
FIG. 4 is a block diagram of an exemplary computer system that may be used to carry out one or more of the methods described herein.

Moving now to FIG. 4 there is shown a block diagram of an exemplary computer 300 that may be used to implement one or more of the methods described herein. The computer 300 may include a display 302 for viewing system information, and a keyboard 304 and pointing device 306 for data entry, screen navigation, etc. A computer mouse or other device that points to or otherwise identifies a location, action, etc., e.g., by a point and click method or some other method, are examples of a pointing device 306. Alternatively, a touch screen (not shown) may be used in place of the keyboard 304 and pointing device 306. The display 302, keyboard 304 and mouse 306 communicate with a processor via an input/output device 308, such as a video card and/or serial port (e.g., a USB port or the like).

A processor 310, such as an AMD Athlon 64® processor or an Intel Pentium IV® processor, combined with a memory 312 execute programs to perform various functions, such as data entry, numerical calculations, screen display, system setup, etc. The memory 312 may comprise several devices, including volatile and non-volatile memory components. Accordingly, the memory 312 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 310 and the memory 312 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 314 allows the computer 300 to communicate with other devices.

A person having ordinary skill in the art of computer programming and applications of programming for computer systems would be able in view of the description provided herein to program a computer system 300 to operate and to carry out the functions described herein. Accordingly, details as to the specific programming code have been omitted for the sake of brevity. Also, while software in the memory 312 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A computer implemented method for planning a position and/or a movement trajectory of a medical instrument in a heterogeneous body structure such that the instrument is delivered to a target region in the heterogeneous body structure, comprising:
   providing each of
   a) body structure data corresponding to mechanical properties of the heterogeneous body structure, wherein said mechanical properties influence a movement of the instrument through the heterogeneous body structure due to the mechanical interaction between the instrument and the heterogeneous body structure,
   b) instrument data concerning mechanical and/or geometric properties of the instrument, and
   c) movement data concerning mechanical properties that are intended to cause and/or describe a movement of the instrument through the heterogeneous body structure; and
   determining, using a processor, the position and/or movement trajectory of the instrument in the heterogeneous body structure to the target region or a probability that said position and/or movement trajectory to the target region will be achieved, wherein said determining is based on the movement data, the body structure data and the instrument data.

2. The method according to claim 1, wherein the medical instrument is a catheter.

3. The method according to claim 1, further comprising calculating a relationship between the position of the instrument in the heterogeneous body structure at the end of the movement and a position of the instrument at the start of the movement based on the movement data, the body structure data and the instrument data.

4. The method according to claim 3, further comprising determining a nominal starting position and/or nominal instrument data that are necessary for the medical instrument to reach the target region, tracking the movement trajectory of the medical instrument and/or increasing a probability of the medical instrument reaching the target region, said determining based on the relationship and a desired position of the medical instrument.

5. The method according to claim 4, further comprising calculating an expected movement trajectory of the instrument in the body structure from the nominal starting position to the target region based on the movement data, the body structure data and the instrument data.

6. The method according to claim 1, wherein providing body structure data includes providing body structure data that determine mechanical properties of the heterogeneous body structure, said mechanical properties including at least one of:
   deviation properties that describe a deviation of the instrument when the instrument contacts a region of the heterogeneous body structure;
   shape-changing properties that describe a change in shape of the instrument when the instrument contacts a region of the heterogeneous body structure;
   blocking properties of the heterogeneous body structure that can stop a forward movement of the instrument in the heterogeneous body structure, wherein the stopping ability corresponds to a penetration depth of the instrument in the body structure; or
   a viscosity of the heterogeneous body structure.

7. The method according to claim 1, wherein providing instrument data includes providing instrument data that determine mechanical properties of the instrument, said mechanical properties including at least one of:
   a malleability of the instrument;
   a geometry, size and/or shape of the instrument; or
   data concerning a material or materials of the instrument.

8. The method according to claim 7, wherein the malleability of the instrument includes at least one of a flexibility, elasticity, rigidity, hardness, distensibility, tensile strength or buckling resistance of the instrument.

9. The method according to claim 1, wherein providing movement data concerning mechanical properties includes providing movement data that determine mechanical properties of the movement, said mechanical properties including at least one of:
   a starting location of the movement;
   a target location of the movement;
   a force that is intended to cause the movement;
   a pressure that is intended to cause the movement;
   a moment that is intended to move the instrument;
   an impulse that is intended to act on the instrument; or
   a movement trajectory that describes a course of the planned movement as the instrument passes through a homogeneous body structure having a predetermined viscosity.

10. The method according to claim 9, wherein the force includes at least one of a direction of the force, a magnitude of the force, or a force vector as a function of time.

11. The method according to claim 9, wherein the pressure includes at least one of a direction of the pressure, a magnitude of the pressure, or a pressure vector as a function of time.

12. The method according to claim 9, wherein the moment includes a torque intended to move the instrument.

13. The method according to claim 9, wherein the moment is a moment vector as a function of time.

14. The method according to claim 9, wherein the impulse is an impulse vector as a function of time.

15. The method according to claim 1, further comprising using the planned position and/or movement trajectory of the instrument to plan an infusion of a drug into the heterogeneous body structure.

16. The method according to claim 1, wherein determining is performed prior to insertion of the medical device into the heterogeneous body structure.

17. The method according to claim 1, further comprising calculating, at least for sections of the movement trajectory, a risk of the medical instrument deviating from the expected movement trajectory or a risk of the medical instrument deviating from a movement channel in which the medical instrument is moved, said calculating based on given tolerances of the at least one of the movement data, body structure data and/or instrument data.

18. A computer implemented method for planning a position and/or a movement trajectory of a medical instrument in a heterogeneous body structure such that the instrument is delivered to a target region in the heterogeneous body structure, comprising:
 providing at least one of
  a) body structure data corresponding to mechanical properties of the heterogeneous body structure, wherein said mechanical properties influence a movement of the instrument through the heterogeneous body structure due to the mechanical interaction between the instrument and the heterogeneous body structure,
  b) instrument data concerning mechanical and/or geometric properties of the instrument, or
  c) movement data concerning mechanical properties that are intended to cause and/or describe a movement of the instrument through the heterogeneous body structure; and
 determining, using a processor, the position and/or movement trajectory of the instrument in the heterogeneous body structure to the target region or a probability that said position and/or movement trajectory to the target region will be achieved, wherein said determining is based on at least one of the movement data, the body structure data or the instrument data, further comprising calculating, at least for sections of the movement trajectory, a risk of the medical instrument deviating from the expected movement trajectory or a risk of the medical instrument deviating from a movement channel in which the medical instrument is moved, said calculating based on given tolerances of the at least one of the movement data, body structure data and/or instrument data.

19. A computer program embodied on a non-transitory computer readable medium for planning a position and/or a movement trajectory of a medical instrument in a heterogeneous body structure such that the instrument is delivered to a target region in the heterogeneous body structure, comprising:
 code that provides each of:
  a) body structure data corresponding to mechanical properties of the heterogeneous body structure, wherein said mechanical properties influence a movement of the instrument through the heterogeneous body structure due to the mechanical interaction between the instrument and the heterogeneous body structure;
  b) instrument data concerning mechanical and/or geometric properties of the instrument; and
  c) movement data concerning mechanical properties that are intended to cause and/or describe a movement of the instrument through the heterogeneous body structure; and
 code that determines the position and/or movement trajectory of the instrument in the heterogeneous body structure to the target region or a probability that said position and/or movement trajectory to the target region will be achieved, wherein said determining is based on the movement data, the body structure data and the instrument data.

20. A device for planning a position and/or a movement trajectory of a medical instrument in a heterogeneous body structure such that the instrument is delivered to a target region in the heterogeneous body structure, comprising:
 a processor and memory; and
 logic stored in the memory and executable by the processor, said logic including
  a) logic configured to provide the body structure data corresponding to mechanical properties of the heterogeneous body structure, wherein said mechanical properties influence a movement of the instrument through the heterogeneous body structure due to the mechanical interaction between the instrument and the heterogeneous body structure,
  b) logic configured to provide the instrument data concerning mechanical and/or geometric properties of the instrument, and
  c) logic configured to provide the movement data concerning mechanical properties that are intended to cause and/or describe a movement of the instrument through the heterogeneous body structure; and
 logic configured to determine the position and/or movement trajectory of the instrument in the heterogeneous body structure to the target region or a probability that said position and/or movement trajectory to the target region will be achieved, wherein said determining is based on the movement data, body structure data and instrument data.

21. The device according to claim 20, further comprising a guiding device operative to mechanically guide the instrument through the heterogeneous body structure in accordance with the movement trajectory.

22. The device according to claim 20, further comprising a selection device operative to automatically select a suitable instrument from a given set of instruments.

23. The device according to claim 21, wherein the guiding device comprises a robot operative to guide the movement of the instrument in accordance with the movement trajectory.

* * * * *